(12) United States Patent
Jamali

(10) Patent No.: US 10,105,146 B2
(45) Date of Patent: Oct. 23, 2018

(54) BONE CUTTING GUIDE SYSTEM FOR OSTEOCHONDRAL TRANSPLANTATION

(71) Applicant: Amir A. Jamali, Berkeley, CA (US)

(72) Inventor: Amir A. Jamali, Berkeley, CA (US)

( * ) Notice: Subject to any disclaimer, the term of this patent is extended or adjusted under 35 U.S.C. 154(b) by 605 days.

(21) Appl. No.: 14/673,636

(22) Filed: Mar. 30, 2015

(65) Prior Publication Data

US 2015/0272594 A1    Oct. 1, 2015

Related U.S. Application Data

(60) Provisional application No. 61/972,376, filed on Mar. 30, 2014.

(51) Int. Cl.
*A61B 17/15* (2006.01)
*A61B 17/17* (2006.01)
*A61B 17/16* (2006.01)

(52) U.S. Cl.
CPC ........ *A61B 17/155* (2013.01); *A61B 17/1635* (2013.01); *A61B 17/1764* (2013.01)

(58) Field of Classification Search
CPC ... A61B 17/154; A61B 17/155; A61B 17/157; A61B 17/1735; A61B 17/1764; A61F 2/3859; A61F 2/389
See application file for complete search history.

(56) References Cited

U.S. PATENT DOCUMENTS

| 2012/0209276 A1* | 8/2012 | Schuster | A61B 17/155 606/88 |
| 2014/0243834 A1* | 8/2014 | Chaney | A61F 2/3859 606/88 |

* cited by examiner

*Primary Examiner* — Kevin T Truong
*Assistant Examiner* — Tracy Kamikawa
(74) *Attorney, Agent, or Firm* — Craig M. Stainbrook; Stainbrook & Stainbrook, LLP

(57) ABSTRACT

A bone cutting guide for osteochondral transplantation, including a cutting guide block having a distal portion and a posterior portion, said distal portion having a distal cutting guide slot disposed therethrough, said posterior portion having a posterior cutting guide slot disposed therethrough; a plurality of condylar rails attached to said cutting guide block; a tower cutting guide disposed superior to said cutting guide block and having at least one cutting guide track disposed at an angle of between 0 and 180 degrees in relation to the angle of said posterior cutting guide slot; and fixation structure for attaching said cutting guide block and said tower cutting block to bone.

18 Claims, 9 Drawing Sheets

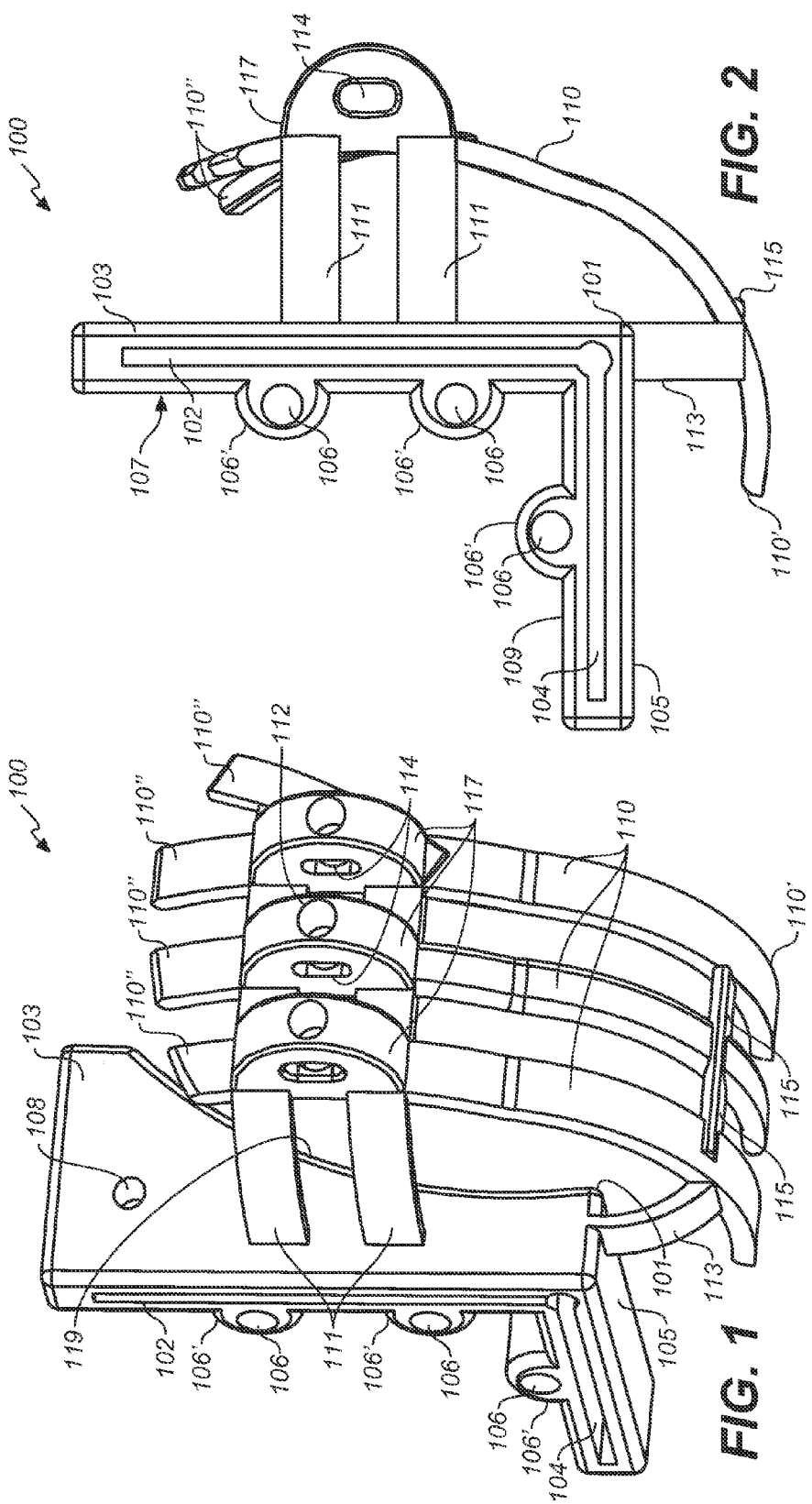

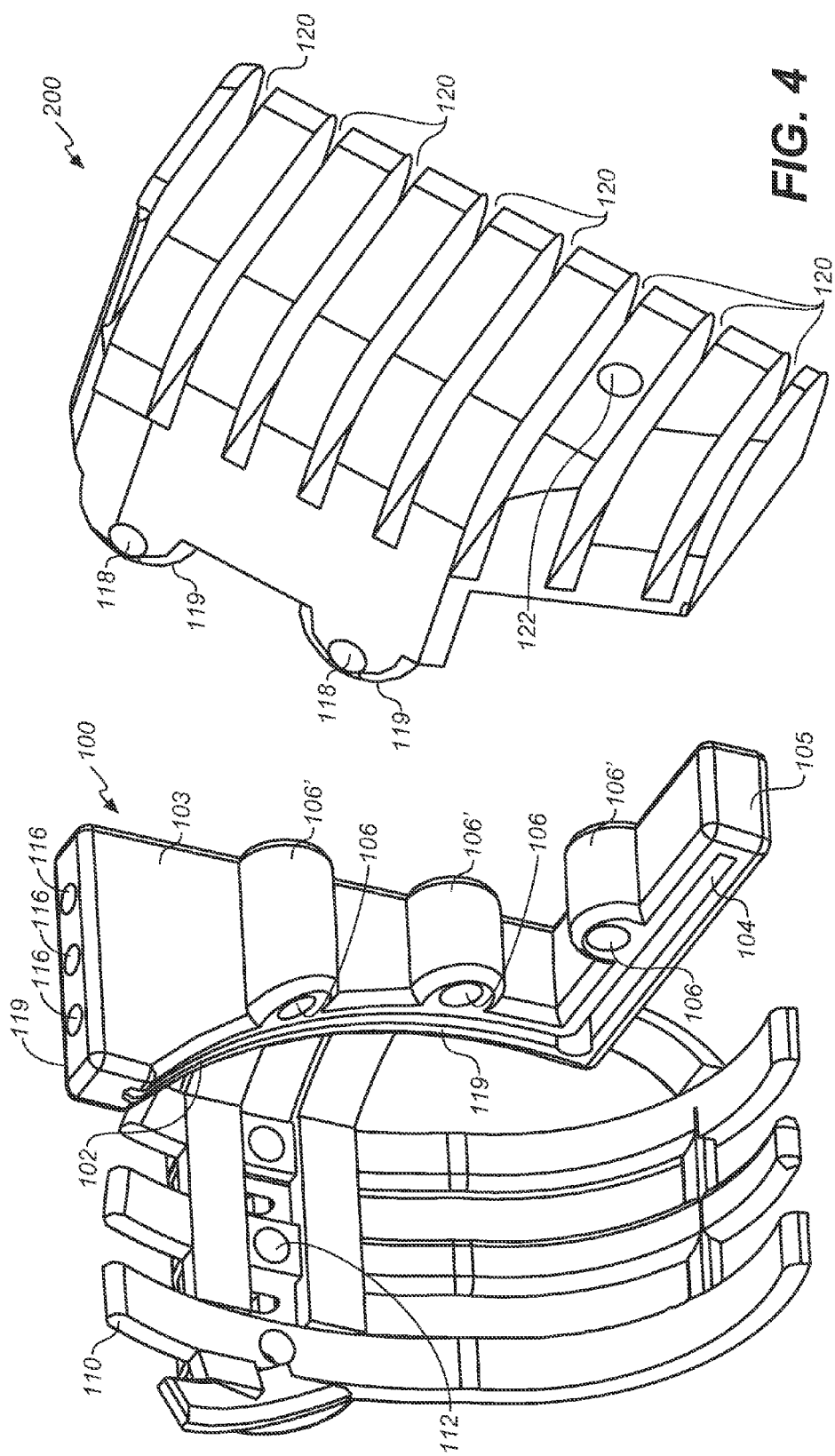

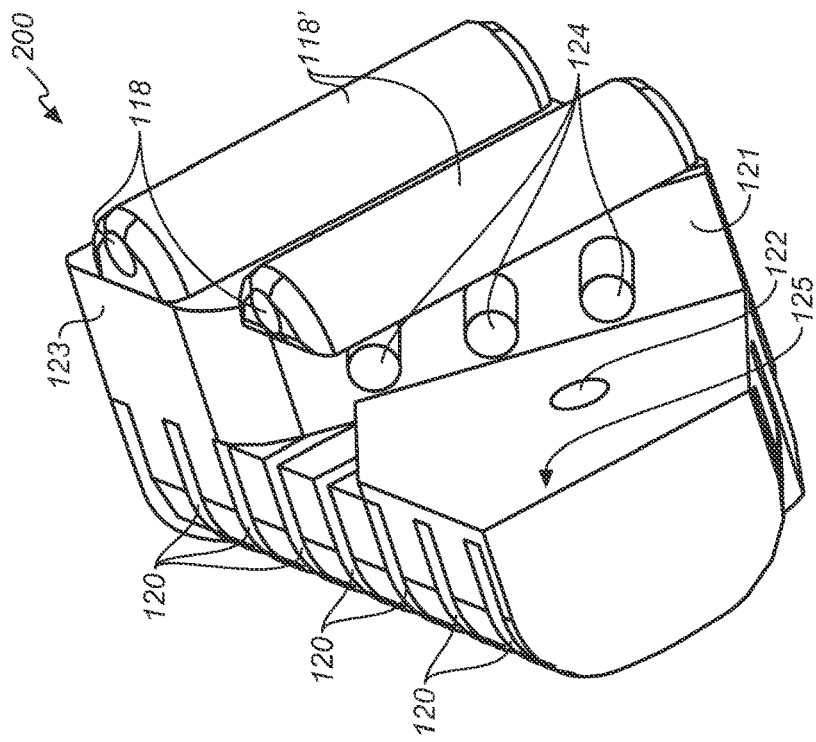
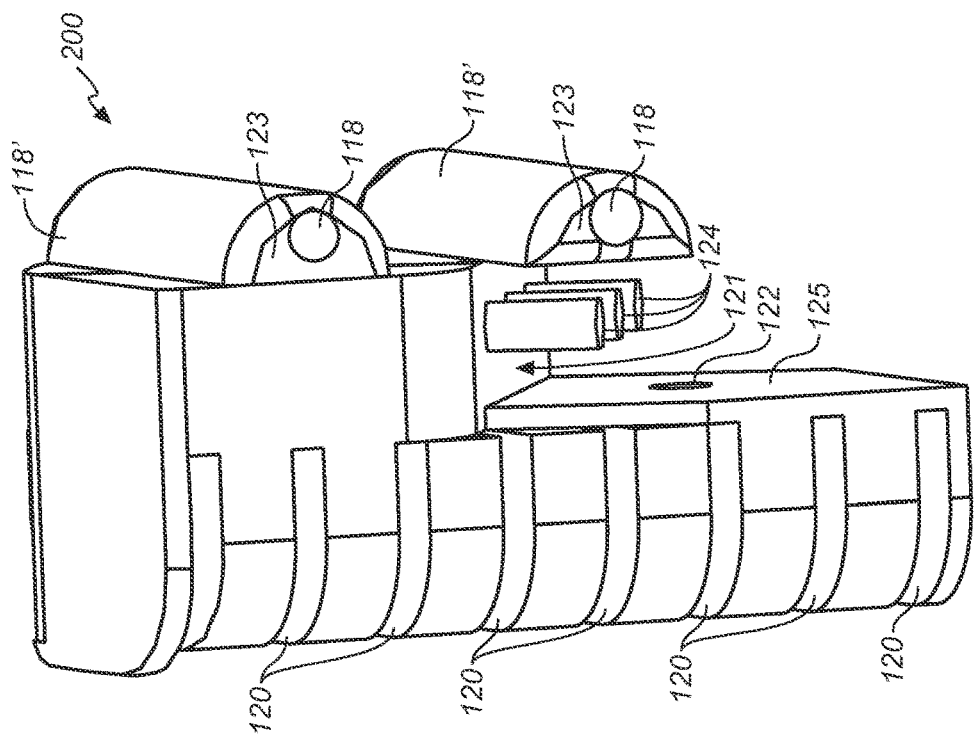

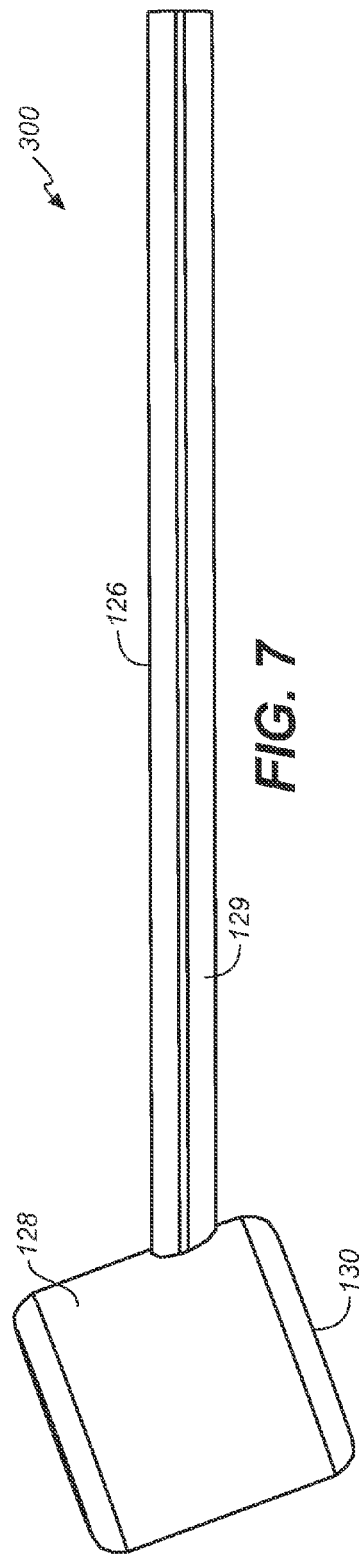
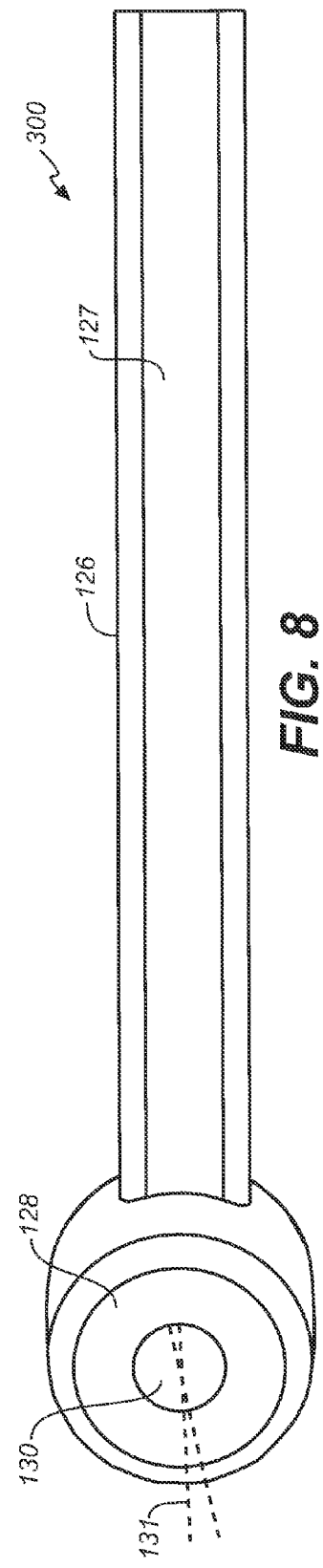

BONE CUTTING GUIDE SYSTEM FOR OSTEOCHONDRAL TRANSPLANTATION

CROSS REFERENCES TO RELATED APPLICATIONS

The present application claims the benefit of U.S. Provisional Patent Application Ser. No. 61/972,376, filed Mar. 30, 2014, which application is incorporated in its entirety by reference herein.

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION BY REFERENCE OF MATERIAL SUBMITTED ON A COMPACT DISC

Not applicable.

BACKGROUND OF THE INVENTION

Field of the Invention

The present invention relates generally to orthopedic medical devices and methods, and more particularly to methods and apparatus for bone transplantation, and more particularly still to a device and technique for preparing and transplanting osteochondral segments in bone using an angular cutting device attached to the surface of the articular cartilage and thus referencing this surface on both the donor and recipient sites.

Background Discussion

Current osteochondral allograft technology provides an unsatisfactory solution to the problem of preparing large osteochondral allografts. The state of the art is limited to the use either of hand instruments, such as saws and burrs or, alternatively, large coring devices. When faced with a large bone defect, for instance one involving the entire condyle, the orthopedic surgeon must use multiple interlocking cylindrical cores to resurface the large surface area. This can be problematic because of the increased graft tissue necessary for an interlocking technique. For example, in order to resurface one femoral condyle, a surgeon might require the donor allograft to include an entire distal femur with both condyles. The cost of such a large graft can be prohibitive to the performance of this type of surgery.

BRIEF SUMMARY OF THE INVENTION

The inventive device and method facilitates the precise preparation of both the donor and recipient bone in such a way that a large bone segment can be fit at the exact height and in direct contact with the patient's own native bone thus restoring the articular surface of a joint. The key elements of the device are the articular rails, platforms, or sliders which rest on the articular surface (hereafter referred to as rails). The rails are contoured to the bony surface to be prepared. Within this block, there is a slot at a predetermined distance away from the articular rails and thus the articular surface. This cutting slot allows the passage of a saw blade in such a way to remove the bone segment either from the donor graft or from the recipient in such a way that both the removed donor and recipient grafts are of the same overall dimensions. When the graft is placed in the recipient site of the patient, it thus restores the articular surface to the desired level with healthy articular cartilage. In order to assist the completion of any additional angular cuts, additional guides and fixation devices can be attached to the cutting guide. In the disclosed rendition of the invention, a separate attachable tower is mounted on the original cutting jig. This attachable tower facilitates the precise cutting of the diseased femoral condyle or femoral condyle graft away from the associated femoral trochlea. Once the graft had been applied into its recipient site it achieves initial stabilization to the bone through direct contact and friction between the posterior condyle, the distal condyle, and the anterior wall of the trochlea. Additional fixation is achieved with standard screws and plates as needed and as commonly practiced in the art of orthopedic surgery. The above described guides can be used alone or in combination to allow transplantation of either one or both femoral condyles. Furthermore, the guides can be utilized with a separate attached trochlear tower which rests on the two femoral condylar guides and allows for recovery of the trochlea as a single entity. Alternatively, by utilizing both condylar guides and the trochlear tower, the entire surface of the human knee can be transplanted. Thus the disclosed invention allows transplantation of either or both femoral condyles independently, either femoral condyle with the femoral trochlea, the femoral trochlea in isolation, or potentially, the entire surface of the distal femur if indicated.

BRIEF DESCRIPTION OF SEVERAL VIEWS OF THE DRAWINGS

The invention will be better understood and objects other than those set forth above will become apparent when consideration is given to the following detailed description thereof. Such description makes reference to the annexed drawings, wherein the orientation of the views corresponds to the anatomical position orientations of the inventive apparatus when installed on a femoral condyle (as seen, for instance, in FIGS. 9-10):

FIG. 1 is an inferior right lateral perspective view of the cutting guide of the present invention;

FIG. 2 is right lateral view in elevation thereof;

FIG. 3 is a superior and medial perspective view thereof;

FIG. 4 is an inferior and right lateral perspective view of the attachable tower cutting guide of the present invention;

FIG. 5 is a lateral (medial) perspective view thereof;

FIG. 6 is an inferior medial perspective view thereof;

FIG. 7 is a lateral view in elevation of a screw guide, including a guide positioning arm, guide body, and screw aperture;

FIG. 8 is the anterior to posterior view in elevation thereof;

DETAILED DESCRIPTION OF THE INVENTION

Figure 9:
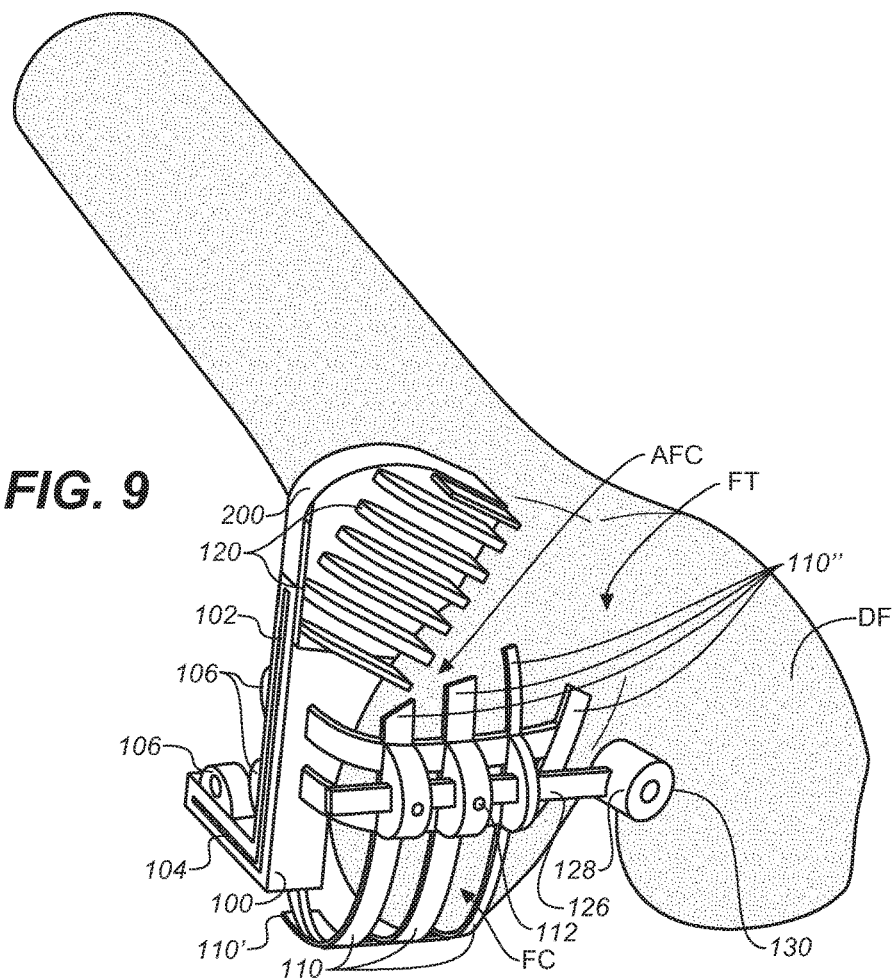
FIG. 9 is an inferior lateral perspective view of the assembled instrument complex applied to a right human distal femoral condyle (i.e. viewed anatomically from distal to proximal and slightly superiorly.

Referring to FIGS. 1 through 17, wherein like reference numerals refer to like components in the various views, there is illustrated therein a new and improved bone cutting guide system for osteochondral transplantation.

Referring first to FIGS. 1-2, cutting guide 100 is seen to comprise a cutting guide block 101 including a distal portion 103 and a posterior portion 105 generally normal to the anterior portion. A distal cutting slot 102 is disposed through the distal portion 103 of the cutting guide block 101 and a posterior cutting slot 104 is disposed through the posterior portion 105. Fixation holes 106 for the guide are shown on both the distal and posterior portions and are preferably disposed through semi-cylindrical bosses 106' or other structure integral with, respectively, the posterior side 107 of the distal portion and the superior side 109 of the posterior portion. A fixation through hole 108 is provided in the distal portion for mounting and securing an attachable tower (discussed more fully below). The cutting guide block distal and posterior portions may be generally planar on their exposed surfaces, though such a configuration is not essential to the operability of the assembly.

At least one condylar rail, and preferably a plurality of spaced apart and generally parallel condylar rails 110, are attached to both the distal and posterior portions of the cutting guide block, the former with at least one, and preferably two, cross bars 111; and the latter with a single strut 113. A lower cross bar 115 provides structural support proximate the lower ends of the condylar rails and may extend so as to be contiguous with strut 113, or it may be a discrete cross-bar structure.

The condylar rails are configured with a curvature to rest on the distal femoral cartilage. Along the distal aspect of the guide and disposed on the outer surfaces of the condylar rails are one or more screw guide bosses 117 having screw guide tracks or apertures 114 disposed therethrough, into and through which a screw guide passes and slides, such that the screw guide is disposed generally transversely across and in front of (distally in relation to) the condylar rails. At least one stabilization bolt hole 112, (bolt not shown) is provided through one or more of the screw guide bosses for placement of a bolt to securing and stabilize the screw guide within the screw guide bosses and within the screw guide track 114. The screw guide is slidably adjustable within the screw guide track for precise positioning on the bone.

It will be seen that the condylar rails include curvature that extends so as to provide a lower posterior rail portion 110' engaging the posterior cartilage surface when in place, and similarly include curvature so as to provide an anterior rail portion 110".

It will be recognized that the cutting guide block 101 is configured with curvature 101' on the condyle-engaging side (though the curvature may be either medial or lateral) of the cutting guide block in the condyle capturing region of the condylar rails so as to closely engage the distal femoral condyle when surgically placed.

Referring next to FIG. 3, which is a posterior lateral perspective view of the cutting guide, there is shown the distal cutting slot 102 in cutting guide block 101. The posterior cutting slot is shown by 104. Fixation holes 106 in the guide are shown and are seen to be through holes. The anterior condylar rail portions 110" rest on the anterior, distal bone surface to be cut. The screw hole 112 for stabilization of the screw guide is shown. The anterior condylar rail portions 110" extends so as to provide a posterior rail portion that rests on the posterior bone condyle. The anterior cylindrical female elements 116 of the cutting guide are shown disposed in the anterior edge 119 of the anterior portion 103 of the cutting guide block 101. This is the docking or attachment site of the attachable tower cutting guide shown in FIGS. 4-6.

FIG. 4 is a perspective view of the attachable tower cutting guide 200 demonstrating the lateral or outer surface 201 with the entry site of the obliquely oriented pin holes 118 for attachment of the guide to the bone. Multiple cutting tracks 120 aligned in a generally parallel array and disposed at a specified angle θ relative to the condylar rails when installed may be employed depending on the specific size of the desired bony cut and the desired anterior to posterior dimension of the femoral condylar graft to be transplanted. An anterior to posterior peg hole 122, is available for engaging attachable tower cutting guide to the cutting guide block 101 by placement of a metal peg through the peg hole and into the fixation hole 108 of the cutting guide block 101.

FIG. 5 is a lateral perspective view of the attachable tower cutting guide 200 demonstrating the inner surface 123 with the exit site of the obliquely oriented pin holes 118 for attachment of the guide to the bone. Multiple cutting tracks 120 are again seen based on the specific size of the desired bone cut. The inner exit site of the anterior to posterior peg hole 122, is shown on the surface 125 that engages the distal portion 103 of the main cutting guide block 101 by placement of a metal peg through the peg hole and into the fixation hole 108 for the cutting guide block 101 of the main cutting guide 100.

FIG. 6 is an inferior perspective view of the attachable tower cutting guide 200 demonstrating the inner surface 123 with the exit site of the obliquely oriented pin holes 118 for attachment of the attachable tower cutting guide to the bone. Again, pin holes 118 are through holes and are disposed in sleeves 118', which may be semi-cylindrical, though geometry is not critical. Multiple cutting tracks 120 are again seen. The proximal exit site of the anterior to posterior peg hole 122 is again shown. Male pedestals 124 are shown to extend from the undersurface 121 of the attachable tower cutting guide for insertion into the superior cylindrical female elements 116 of the distal portion 103 of the main cutting guide block 101.

FIG. 7 is the lateral view of the screw guide 300 showing that it includes an elongate guide positioning arm 126, a generally cylindrical screw guide body 128, and screw aperture 130 disposed through the guide body. The guide positioning arm 126 fits into the screw guide tracks 114, seen in FIGS. 1-2. As can be seen, the cross-sectional shape of the guide positioning arm 126 is generally rectangular and it is sized slightly smaller than the conforming rectangular aperture of the screw guide tracks 114 so as to slide easily and smoothly into and through the aligned screw guide tracks while minimizing lateral movement. Preferably the plane of the larger rectangular dimension 127 is oriented normal to the axis 131 of the screw aperture 130, while the plane of the shorter rectangular dimension 129 is oriented generally parallel to the same axis.

FIG. 8 is the anterior to posterior view of the screw guide, again showing the elongate guide positioning arm 126, the guide body 128, and the screw aperture 130.

FIG. 9 is a perspective view of the entire instrument complex—cutting guide 100 and attachable tower cutting guide 200—as applied to a human distal femur DF. The main cutting guide 100 is shown with its distal cutting slot 102, and its posterior cutting slot 104. Fixation holes 106 in the main cutting guide demonstrate the contact with the femoral condyle FC for passage of the fixation pins (not shown). The condylar rails 110 rest on the anterior femoral condyle AFC and the femoral trochlea FT, and extend along the articular surface. Along the distal aspect, bolt hole 112 (bolt not shown) is provided for passage and insertion of a stabilizing bolt for stabilizing and securing the screw guide positioning arm 126 within the screw guide track 114. The screw guide body 128, and screw aperture 130 are shown and indicate the utility of the sliding positioning arm in allowing appropriate positioning of the screw away from the articular cartilage surface of the femoral condyle 132, as needed, based on the width of the condyle. The attachable tower guide 200 is shown and demonstrates the multiple cutting tracks 120, available for cutting of the condyle-trochlear interface of the diseased distal femur or the femoral allograft. The selected cutting track dictates the anterior-to-posterior length of the femoral graft and must be exactly matched between the recipient and the donor to ensure appropriate sizing of the graft.

Figure 10:
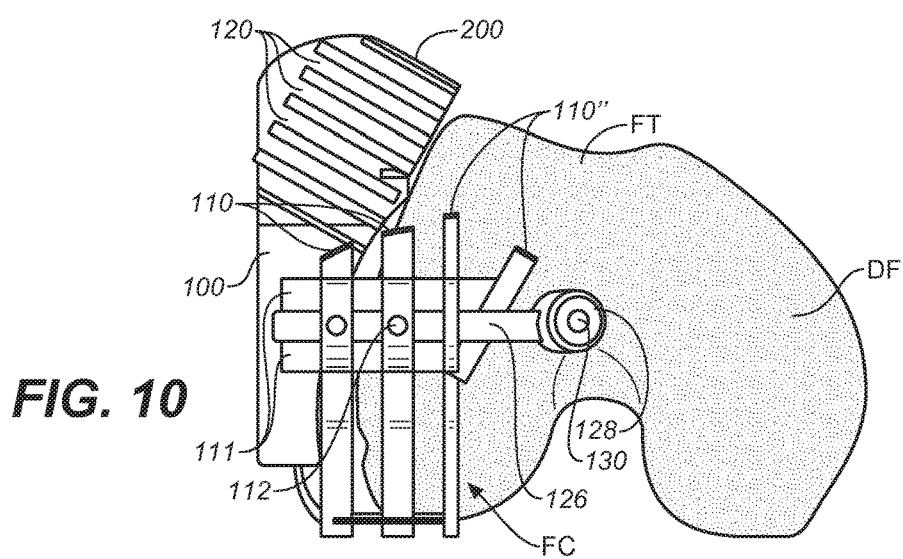
FIG. 10 is an inferior view in elevation thereof.

FIG. 10 is a distal view of the entire instrument complex as applied to a human distal femoral condyle FC. The femoral condylar cutting guide is shown with its condylar rails 110, resting on the anterior femoral condyle and trochlea and extending posteriorly along the articular surface. At the distal most aspect of the guide there is a track 114, (not shown) for the screw guide positioning arm 126, with the bolt hole 112, (bolt not shown) for stabilization of the screw guide positioning arm 126. The screw guide body 128, and screw aperture 130 are shown. The trochlear cutting guide is shown and demonstrates the multiple cutting tracks, 120 available for cutting of the trochlear interface of the femoral allograft.

Figure 11:
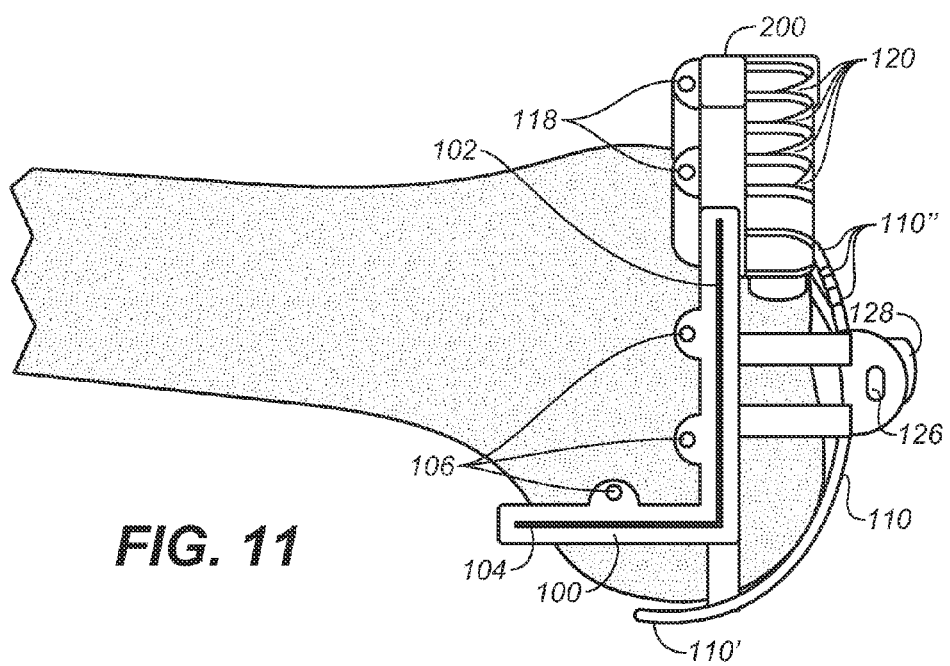
FIG. 11 is a right lateral view in elevation thereof.

FIG. 11 is a lateral view of the entire instrument complex as applied to a human distal femur. The main cutting guide is shown with its condylar rails 110, resting on the femoral condyle and trochlea. At the distal most aspect of the guide the track for the screw guide positioning arm 126 is shown, along with the screw guide body 128. The attachable tower cutting guide 200 is shown and again demonstrates the multiple cutting tracks 120 available for cutting of the trochlear interface of the femoral allograft. Attached to the proximal aspect of the attachable tower cutting guide, there are obliquely oriented pin holes for attachment of the guide to the bone 118.

Figure 12:
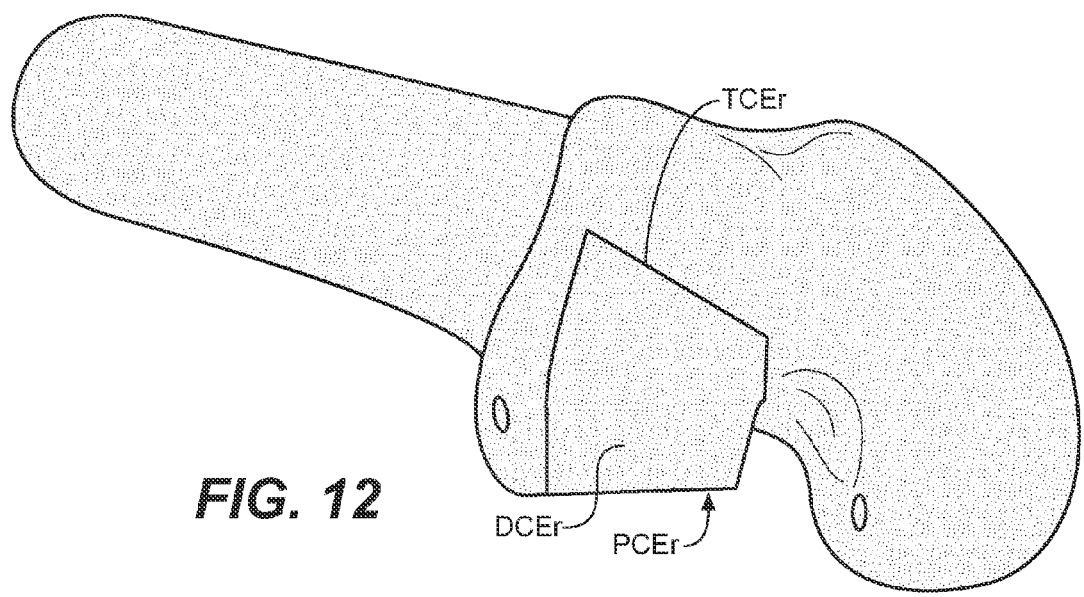
FIG. 12 is a perspective view of the patient's left femur after removal of the diseased medial femoral condyle so as to form the patient's femoral condyle recipient site.

FIG. 12 is a perspective view of a recipient patient's femur after removal of the diseased femoral condyle. Shown is the distal femoral cut edge DCEr, the trochlear cut edge TCEr, and the posterior femoral condyle cut edge PCEr.

Figure 13:
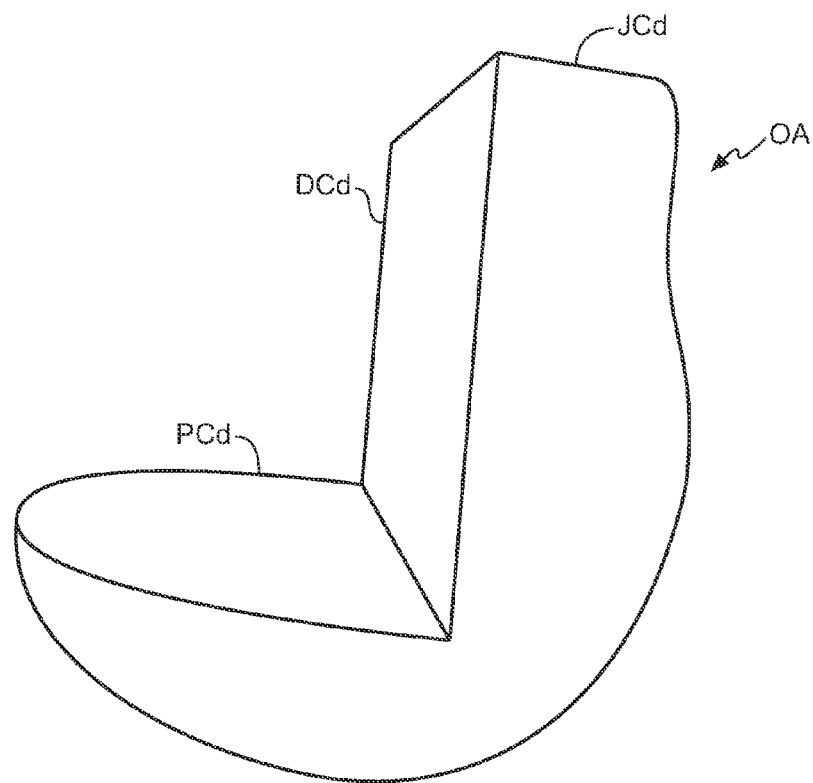
FIG. 13 is a lateral view of a femoral condyle osteochondral allograft after removal from the entire distal femoral allograft.

FIG. 13 is a lateral view of the donor's femoral condyle osteochondral allograft OA after it has been removed from the graft and indicating the position of the trochlear cut TCd, the distal femoral cut DCd, and the posterior condylar cut PCd.

Figure 14:
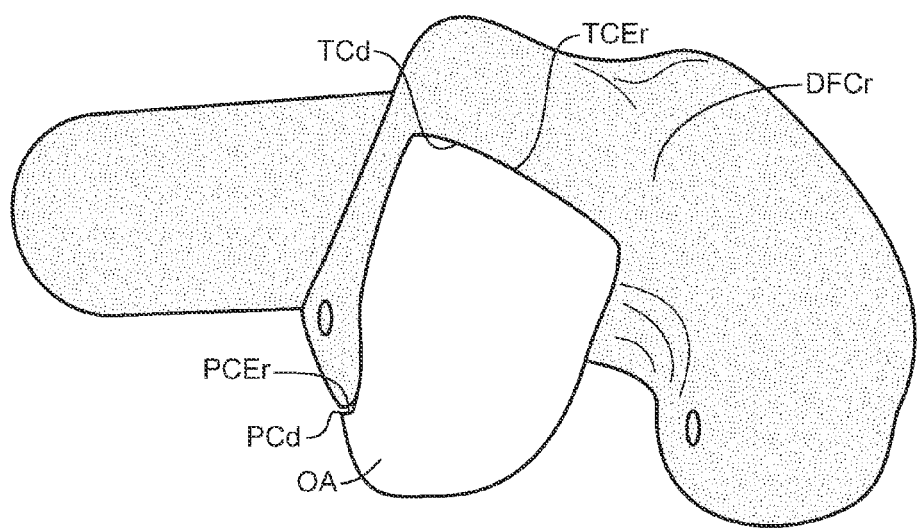
FIG. 14 is a perspective view of the osteochondral allograft after placement on the distal end of the patient's femoral condyle recipient site.

FIG. 14 is a perspective view of the osteochondral allograft after it has been placed on the distal end of the patient's distal femoral condyle recipient site. The patient's distal femur DF, is shown. The cut trochlear edge TCEr is indicated as well as the posterior condylar edge PCEr.

Figure 15:
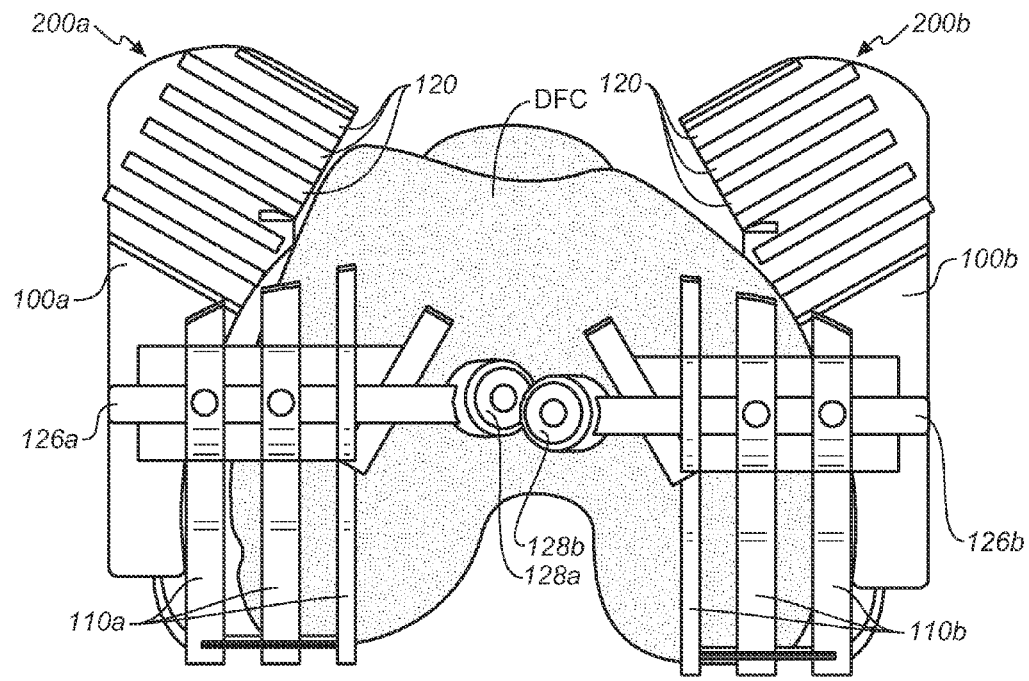
FIG. 15 is a right lateral view in elevation of symmetrical (mirror image) guides applied to the end of a distal femur taken from the same perspective as that of FIG. 11.

FIG. 15 is a distal view of two mirror image (medial and lateral) guides applied to the end of the distal femur. They can each be stabilized to their independent femoral condyle with an independent locking screw guide 128a and 128b. The trochlea can be prepared using the attachable tower cutting guide as shown 200a and 200b.

Figure 16:
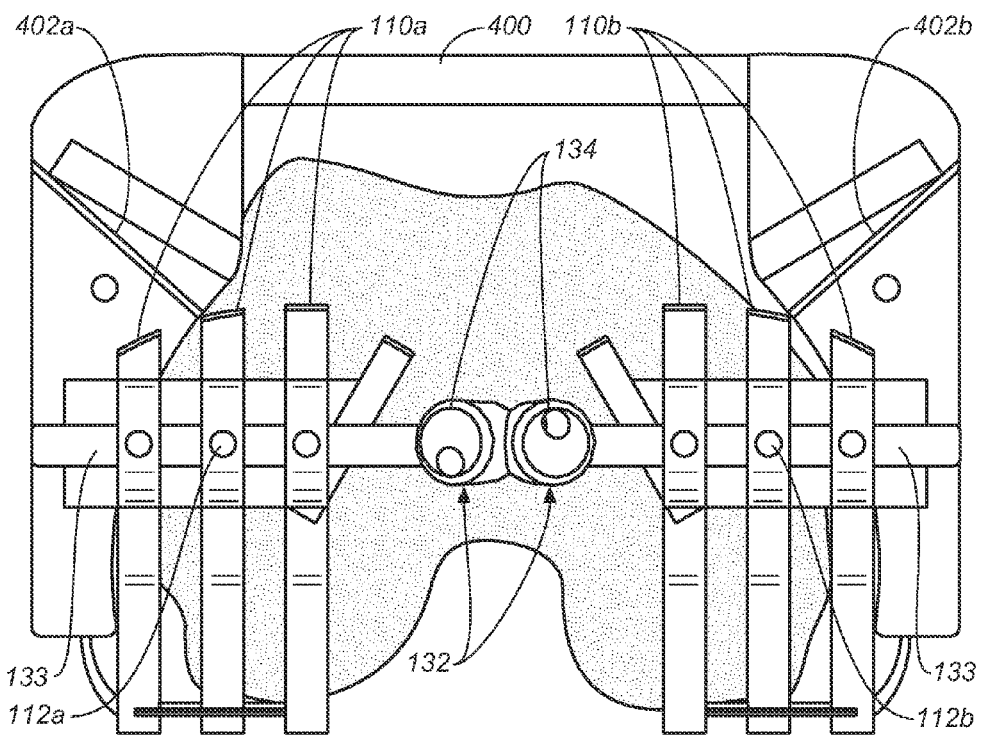
FIG. 16 is a front view in elevation of the symmetrical (mirror image) guides applied to the end of the distal femur, and further including a mounted monoblock trochlear harvesting guide.

FIG. 16 is a distal view of two mirror image cutting guides 100a, 100b, applied to the end of the distal femur DF. An alternative embodiment is shown for a single block trochlear guide 400 which rests on the two condylar guides. The condylar guides are shown with their condylar rails 110a, 110b, and bolt holes 112a, 112b, which in this case are holding a single rigid connection rod 132 consisting of two attached screw guide bodies 134 in the midportion of an extended guide positioning arm 133. The rigid connection rod maintains the two mirror image guides in a collinear orientation facilitating the precision of the procedure.

The trochlear guide consists of angled cutting surfaces 402A and 402b, which are disposed in angular deviations between 0 degrees and 180 degrees between the two sides. The single block trochlear guide facilitates en bloc removal of the diseased trochlea and harvesting of an identically sized osteochondral allograft trochlea.

Figure 17:
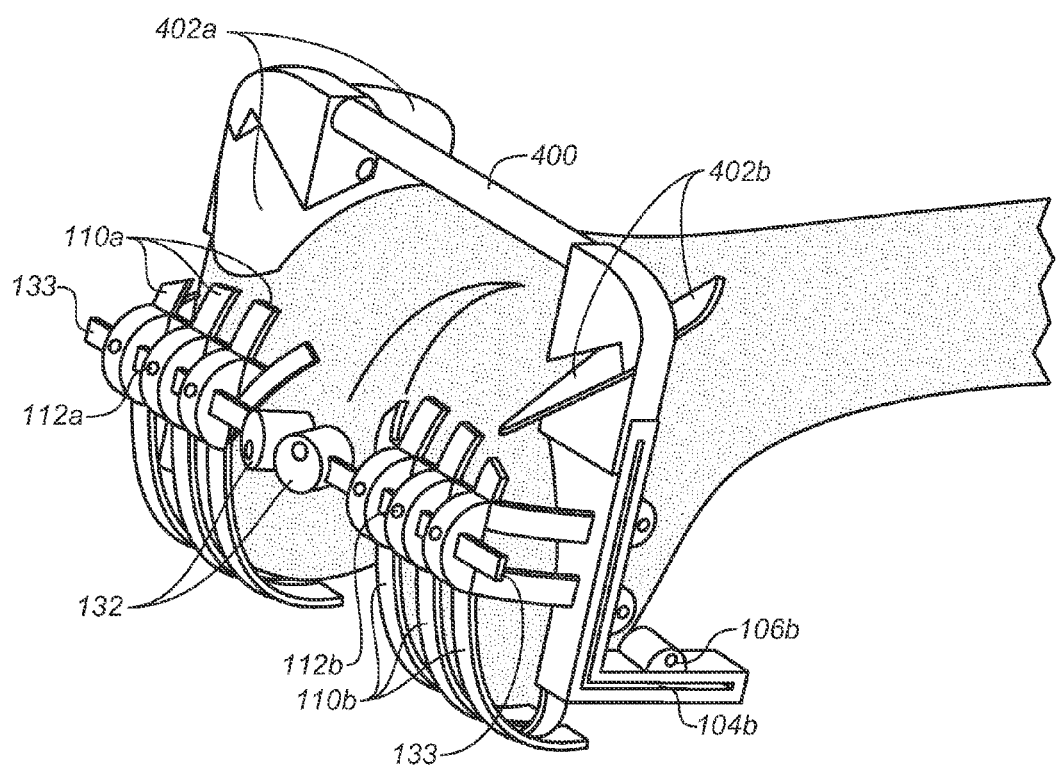
FIG. 17 is an upper front right perspective view of the symmetrical (mirror image) guides applied to the end of the distal femur with the mounted monoblock trochlear harvesting guide also installed.

FIG. 17 is a distal perspective view of the apparatus from FIG. 16 showing the condylar guides with their condylar rails 110a, 110b, respectively, and corresponding bolt holes 112a, 112b, for holding the rigid connection rod 132 with its extended guide positioning arms 133, and the single block trochlear guide 400 with its angled cutting surfaces 402a, 402b. The posterior cutting slot 104b and fixation hole 106b of the condylar guide are also shown.

Various preferred embodiments of the invention have been described in fulfillment of the various objects of the invention. It will be recognized by those with skill in the art that these embodiments are merely illustrative of the principles of the invention. Numerous modifications and adaptations thereof will be readily apparent those skilled in the art without departing from the spirit and scope of the invention. The above-described surgical device and the techniques for using it can be applied to a wide variety of joints and are not limited to application in the human knee. Therefore, the above description and illustrations should not be construed as limiting the scope of the invention, which is defined by the appended claims.

What is claimed as invention is:

1. A bone cutting guide for osteochondral allograft transplantation, comprising:
   a cutting guide block having a distal portion and a posterior portion, said distal portion having a distal cutting guide slot disposed therethrough that is elongated along a generally posterior to anterior direction, said posterior portion having a posterior cutting guide slot disposed therethrough that is elongated along a generally distal to proximal direction;
   one or more arcuate condylar rails attached to said cutting guide block and configured to be positioned at least partially distally of the bone;

a tower cutting guide selectively and removably attached to and disposed anterior to said cutting guide block and having at least one cutting guide track disposed at an angle of between 0 and 180 degrees in relation to said posterior cutting guide slot; and a fixation structure for attaching said cutting guide block to the bone;

wherein said cutting guide slots in each of said distal portion and said posterior portion of said cutting guide block, and said cutting guide track in said tower cutting guide, are each configured to be positioned proximally and at least partially laterally in relation to said condylar rails so as to allow passage of a surgical cutting tool through said cutting guide slots and said cutting guide track from a side of the bone without contacting said condylar rails, wherein said bone cutting guide is configured to prepare both a donor site and a recipient site, with the cuts made therethrough thereby permitting both removal of a monoblock bone allograft from the donor site and thereafter removal of diseased bone from the recipient site for placement of the donor bone allograft, in such a manner that the removed donor bone allograft and the recipient site are of the same overall dimensions.

2. The bone cutting guide of claim 1, wherein said bone cutting guide is configured to engage the distal end of a human bone at the articular edge and rest on the articular surface.

3. The bone cutting guide of claim 1, wherein said surgical cutting tool may include a saw, a cutting chisel, or a motorized burr.

4. The bone cutting guide of claim 1, wherein said one or more condylar rails are configured to rest on the articular surface of the bone.

5. The bone cutting guide of claim 1, wherein said one or more condylar rails are configured to engage both the posterior and distal portions of a distal femoral condyle.

6. The bone cutting guide of claim 1, wherein said cutting guide slots are separated from said one or more condylar rails in a range between 1 mm and 100 mm so as to fit a particular human joint.

7. The bone cutting guide of claim 1 wherein said fixation structure comprises a plurality of guide holes separated at distances of between 5 to 50 mm for stabilization of the guide to the bone in the desired position.

8. The bone cutting guide of claim 7, wherein said guide holes are disposed through bosses integral with the cutting guide block.

9. The bone cutting guide of claim 1, further including a screw guide track disposed transversely across said one or more condylar rails and a locking screw guide, said locking screw guide having an elongate arm for slidable insertion into said screw guide track and a screw guide body disposed at one end of said elongate arm and having a bolt hole for passage of a bone screw, such that said locking screw guide is adjustably slidable laterally across the bone and selectively lockable within said screw guide track for adjustable fixation to the bone.

10. The bone cutting guide of claim 1, wherein said distal portion is generally normal to said posterior portion.

11. The bone cutting guide of claim 1, wherein said one or more condylar rails are attached to said posterior portion of said cutting guide block with a strut and to said distal portion of said cutting guide block with at least one cross bar.

12. The bone cutting guide of claim 11, further including a lower cross bar disposed between two of said one or more condylar rails proximate a lower posterior rail portion of said one or more condylar rails.

13. The bone cutting guide of claim 1, wherein said cutting guide block includes a through hole for passage of a pin or peg to secure said tower cutting guide to said cutting guide block.

14. The bone cutting guide of claim 1, wherein said at least one cutting guide track includes a plurality of cutting guide tracks in said tower cutting guide, wherein said cutting guide tracks when viewed in the distal to proximal direction are aligned in a generally parallel array and disposed at a slight angle relative to said one or more condylar rails.

15. A bone cutting guide for osteochondral transplantation, comprising:

medial and lateral symmetrically configured cutting guide blocks, each cutting guide block having a distal portion and a posterior portion, each distal portion having a distal cutting guide slot disposed therethrough that is elongated along a generally posterior to anterior direction, each posterior portion having a posterior cutting guide slot disposed therethrough that is elongated along a generally distal to proximal direction;

one or more arcuate condylar rails attached to each of said medial and lateral cutting guide blocks and configured to be positioned at least partially distally of the bone;

a medial tower cutting guide and a lateral tower cutting guide, each selectively and removably attached to and disposed anterior to a respective cutting guide block and having at least one cutting guide track disposed at an angle of between 0 and 180 degrees in relation to its respective said posterior cutting guide slot; and a fixation structure for attaching each of said cutting guide blocks and said tower cutting guides to the bone;

wherein said cutting guide slots in each of said distal portion and said posterior portion of each said cutting guide block, and said cutting guide track in each said tower cutting guide, are each configured to be positioned proximally and at least partially laterally in relation to said respective condylar rails so as to allow passage of a surgical cutting tool through said cutting guide slots and said cutting guide tracks from a respective side of the bone without contacting said respective condylar rails, wherein said bone cutting guide is configured to prepare both a donor site and a recipient site, with the cuts made therethrough thereby permitting both removal of a monoblock bone allograft from the donor site and thereafter removal of diseased bone from the recipient site for placement of the donor bone allograft, in such a manner that the removed donor bone allograft and the recipient site are of the same overall dimensions.

16. The bone cutting guide of claim 15, wherein the medial tower cutting guide and the lateral tower cutting guide comprise a single block tower guide for connecting said medial cutting guide block to said lateral cutting guide block, wherein the single block tower guide is attachable to the anterior surface of each said cutting guide block and spans from one cutting guide block to the other at a fixed length.

17. The bone cutting guide of claim 16, further comprising a screw guide track disposed transversely across each of said one or more condylar rails of each of said medial and lateral cutting guide blocks, and at least one locking screw guide, said at least one locking screw guide having an elongate arm for slidable insertion into said screw guide track and an integral screw guide body and having a bolt hole for passage of a bone screw, such that said locking screw guide is adjustably slidable laterally across the bone and selectively lockable within said screw guide track for adjustable fixation to the bone, such that the distance between said medial cutting guide block and said lateral cutting guide block is slidably adjustable by moving at least one of said cutting guide blocks along the length of said elongate arm.

18. The bone cutting guide of claim 17, wherein said cutting guide tracks of the medial and lateral tower cutting guides have a convergence angle between 90 and 180 degrees.

\* \* \* \* \*